United States Patent
Raines et al.

(10) Patent No.: US 7,858,741 B2
(45) Date of Patent: Dec. 28, 2010

(54) STABILIZATION OF THE COLLAGEN TRIPLE HELIX BY O-METHYLATION OF HYDROXYPROLINE RESIDUES

(75) Inventors: Ronald T. Raines, Madison, WI (US); Frank W. Kotch, Monona, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 155 days.

(21) Appl. No.: 12/367,374

(22) Filed: Feb. 6, 2009

(65) Prior Publication Data

US 2009/0264626 A1    Oct. 22, 2009

Related U.S. Application Data

(60) Provisional application No. 61/026,674, filed on Feb. 6, 2008.

(51) Int. Cl.
  *A61K 38/06* (2006.01)
  *C07K 5/08* (2006.01)

(52) U.S. Cl. .................... 530/331; 530/345; 530/356

(58) Field of Classification Search ................. None
See application file for complete search history.

(56) References Cited

U.S. PATENT DOCUMENTS

| 5,973,112 | A | 10/1999 | Raines |
| 7,122,521 | B2 | 10/2006 | Raines |
| 2007/0275897 | A1 | 11/2007 | Raines |

FOREIGN PATENT DOCUMENTS

WO    WO 2007/039914    12/2007

OTHER PUBLICATIONS

Alabugin and Zeidan, "Stereoelectronic effects and general trends in hyperconjugative acceptor ability of sigma bonds." J. Am. Chem. Soc. 124:3175-3185 (2002).
Bella et. al., "Crystal and molecular structure of a collagen-like peptide at 1.9 A resolution." Science 266: 75-81 (1994).
Bretscher et. al., "Conformational stability of collagen relies on a stereoelectronic effect." J. Am. Chem. Soc. 123:777-778 (2001).
Holmgren et. al., "Code for collagen's stability deciphered." Nature 392:666-667 (1998).
Holmgren et. al., "A hyperstable collagen mimic." Chem. Biol. 6: 63-70 (1999).
Janesko et. al., "Using Vonstrained Schrödinger equations to separate resonant and inductive substituent effects: a new methodology for parametrizing simple models in chemistry." J. Phys. Chem. 107:1655-1663 (2003).
Jenkins and Raines, "Insights on the conformational stability of collagen." Nat. Prod. Rep. 19: 49-59 (2002).
Jenkins et. al., "O-acylation of hydroxyproline residues: effect on peptide-bond isomerization and collagen stability." Biopolymers 80:1-5 (2005).
Kotch et. al., "Stabilization of the collagen triple helix by O-methylation of hydroxyproline residues." J. Am. Chem. Soc. 130:2952-2953 (2008).
Malkar et. al., "Modulation of triple-helical stability and subsequent melanoma cellular responses by single-site substitution of fluoroproline derivatives." Biochemistry 41:6054-6064 (2002).
Miles and Burjanadze, "Thermal stability of collagen fibers in ethylene glycol." Biophys. J. 80:1480-1486 (2001).
Nemethy, "Energetics and thermodynamics of collagen self-assembly." in Collagen, Nimmi (Ed), CRC Press: Boca Raton, FL, pp. 79-94 (1988).
Nishi et. al., "Different effects of 4-hydroxyproline and 4-fluoroproline on the stability of collagen triple helix." Biochemistry 44:6034-6042 (2005).
Okuyama et. al., "Crystal and molecular structure of a collagen-like polypeptide (Pro-Pro-Gly)10." J. Mol. Biol., 152:247-443 (1981).
Periskov et. al., "Triple-helix propensity of hydroxyproline and fluoroproline: Comparison of host—guest and repeating tripeptide collagen models." J. Am. Chem. Soc. 125:11500-11501 (2003).
Raines, "2005 Emil Thomas Kaiser Award." Protein Sci. 15:1219-1225 (2006).
Ramshaw et. al., "Collagen-based biomaterials." Biotechnol. Genet. Eng. Rev., 13, 335-382 (1995).
Sharp, K. A. et al., "Reconciling the magnitude of the microscopic and macroscopic hydrophobic effects." Science 252:106-109 (1991).
Shoulders et. al, "4-chloroprolines: synthesis, conformational analysis, and effect on the collagen triple helix." Biopolymers 89:443-454 (2008).
Hodges, J. A. et al., Stereoelectronic Effects on Collagen Stability: The Dichotomy of 4-Fluoroproline Diastereomers, 2003, J. Am. Chem. Soc., 125:9262-9263.

*Primary Examiner*—Suzanne M. Noakes
(74) *Attorney, Agent, or Firm*—Sara D. Vinarov; Quarles & Brady LLP

(57) ABSTRACT

This invention relates to a collagen polypeptide comprising a tripeptide motif having the formula $(ProYaaGly)_n$, where Yaa is an O-methylated amino acid residue and "n" is the number of motif repeats. Preferred O-methylated amino acid residues at the Yaa position include (2S,4R)-4-methoxyproline. Other suitable amino acid residues at that position include O-mono or O-di-halogenated methylproline. Also, disclosed is a method of making a synthetic or a semi-synthetic collagen polypeptide molecule having increased stability relative to natural collagen. The strengthened collagen molecules are suitable for use in biomaterials for the medical field or in leather-related products prepared by the tanning industry.

21 Claims, 2 Drawing Sheets

STABILIZATION OF THE COLLAGEN TRIPLE HELIX BY O-METHYLATION OF HYDROXYPROLINE RESIDUES

CROSS-REFERENCE TO RELATED APPLICATIONS

This application claims the benefit and priority of U.S. Provisional Application No. 61/026,674 filed Feb. 6, 2008, which is incorporated herein by reference in its entirety.

STATEMENT REGARDING FEDERALLY SPONSORED RESEARCH OR DEVELOPMENT

This invention was made with United States government support awarded by the following agencies: NIH AR044276, AR0508811. The United States government has certain rights in this invention.

BACKGROUND OF THE INVENTION

Collagen is the most abundant protein in vertebrates, occurring in virtually every tissue, including skin, tendon, bone, blood vessel, cartilage, ligament, and teeth. Collagen serves as the fundamental structural protein for vertebrate tissues. Collagen abnormalities are associated with a wide variety of human diseases, including arthritis, rheumatism, brittle bones, atherosclerosis, cirrhosis, and eye cataracts. Collagen is also critically important in wound healing. Increased understanding of the structure of collagen, and of how its structure affects its stability, facilitates the development of new treatments for collagen-related diseases and improved wound healing treatments.

Collagen is a fibrous protein consisting of three polypeptide chains that fold into a triple helix, Jenkins and Raines *Nat. Prod. Rep.* 19: 49-59 (2002). Mammals produce at least 17 distinct polypeptide chains that combine to form at least 10 variants of collagen. In each of these variants, the polypeptide chains of collagen are composed of approximately 300 repeats of the tripeptide sequence Xaa-Yaa-Gly, where the first amino acid, Xaa, is often a proline (Pro) residue, the second amino acid, Yaa, is often a 4(R)-hydroxyproline (Hyp) residue, and the third amino acid is glycine. In connective tissue (such as bone, tendon, cartilage, ligament, skin, blood vessels, and teeth), individual collagen molecules are wound together in tight triple helices. These helices are organized into fibrils of great tensile strength, Jones and Miller, *J. Mol. Biol.*, 218:209-219 (1991). Varying the arrangements and cross linking of the collagen fibrils enables vertebrates to support stress in one-dimension (tendons), two-dimensions (skin), or three-dimensions (cartilage).

In vertebrates, the collagen polypeptide is translated with the typical repeat motif being ProProGly. Subsequently, in vivo, the hydroxylation of Pro residues is performed enzymatically after collagen biosynthesis but before the chains begin to form a triple helix. Thus, hydroxylation could be important for both collagen folding and collagen stability (Raines *Protein Sci.* 15:1219-1225 (2006)). The hydroxyl group of Hyp residues has long been known to increase the thermal stability of triple-helical collagen, Berg and Prockop, *Biochem. Biophys. Res. Comm.*, 52:115-120 (1973). For example, the melting temperature of a triple helix of (ProHypGly)$_{10}$ chains is 58° C., while that of a triple helix of (ProProGly)$_{10}$ chains is only 24° C., see: Sakakibara et. al., *Biochem. Biophys. Acta,* 303:198-202 (1973). In addition, the rate at which (ProHypGly)$_{10}$ chains fold into a triple helix is substantially greater than the corresponding rate for (ProPro-Gly)$_{10}$ chains, see: Chopra and Ananthanarayanan, *Proc. Natl. Acad. Sci. USA,* 79:7180-7184 (1982).

In general, molecular modeling based on the structure of triple-helical collagen and conformational energy calculations suggest that hydrogen bonds cannot form between the hydroxyl group of Hyp residues and any main chain groups of any of the collagen molecules in the same triple helix, see: Okuyama et. al., *J. Mol. Biol.,* 152:247-443 (1981). Also, several models include the hypothesis that hydroxyproline increases the stability of collagen. It is believed that the stability may be a result of a bridge of water molecules formed between the hydroxyl group and a main chain carbonyl group. For reviews of observations advancing this hypothesis, see: Suzuki et. al., *Int. J. Biol. Macromol.,* 2:54-56 (1980), and Némethy, in *Collagen*, published by CRC press (1988), and the references cited therein.

However, there exists experimental evidence that is inconsistent with the "bridge of water molecule" model. For example, the triple helices of (ProProGly)$_{10}$ and (ProHypGly)$_{10}$ were found to be stable in 1,2-propanediol, and Hyp residues conferred added stability in these anhydrous conditions, Engel et. al., *Biopolymers,* 16:601-622 (1977), suggesting that water molecules do not play a part in the added stability of (ProHypGly)$_{10}$. Notably, the frequency of Hyp could be too low to support such a water network in natural collagen. In the strands of human type-I collagen, an Xaa-HypGly sequence occurs in no more than four consecutive triads, and occurs in four consecutive triads only twice over >1000 residues. In addition, heat capacity measurements are inconsistent with collagen having more than one bound water per six Gly-X-Y units, Hoeve and Kakivaya, *J. Phys. Chem.,* 80:754-749 (1976). There exists no prior definitive demonstration of the mechanism by which the hydroxyproline residues stabilize collagen triplexes. Therefore, the molecular basis for these observed effects is still not clear. However, recent structural studies have begun to shed light on the structure and stability of collagen's triple-helix, see Jenkins and Raines (2002).

An alternative to the "bridge of water molecule model" (Bella et. al., *Science* 266: 75-81 (1994)) is that of stereoelectronic effects. It is hypothesized that by using stereoelectronic effects electronegative oxygen preorganizes and places the main chain in the proper conformation for triple-helix formation. (Holmgren et. al., *Nature* 392:666-667 (1998)). The stereoelectronic effect explanation originates from the observation that replacing Hyp with (2S,4R)-4-fluoroproline (Flp) increases triple-helix stability; the fluoro group is strongly electron-withdrawing but cannot participate effectively in a putative hydrogen-bonded network. Similar results have been obtained with (2S,4R)-4-chloroproline. (Shoulders et. al, *Biopolymers* 89:443-454 (2008)). This explanation has been challenged by a host-guest study in which a single Hyp→Flp substitution was shown to destabilize a triple helix. (Periskov et. al., *J. Am. Chem. Soc.* 125:11500-11501 (2003)). A similar study has, however, reported a stabilization. (Malkar et. al., *Biochemistry* 41:6054-6064 (2002)). Therefore, it is still unclear whether Hyp stabilizes collagen by serving as a template for a water network or through stereoelectronic effects. A better understanding of how the structure of collagen contributes to its stability would facilitate the design of a collagen or collagen mimics having improved stability. A highly stable collagen substitute could advance the development of improved wound healing treatments.

In recent years, there have been exciting developments in wound healing, including the development of tissue engineering and tissue welding. For example, autologous epidermal transplantation for the treatment of burns was a significant advance in tissue engineering. Tissue engineering has also led to the development of several types of artificial skin, some of which employ human collagen as a substrate. However, a major problem associated with this treatment is the fragile nature of these grafts during and after surgery.

Tissue welding is a wound healing technique in which a laser is used to thermally denature the collagen in the skin at the periphery of a wound. The wound is reannealed by permitting the renaturation of the collagen. In the case of large wounds, a "filler" or solder is required to effect reannealing of the wound. Various materials, including human albumin, have been used as solders for this purpose. A good solder is resilient and is non-immunogenic and should preferably be capable of interaction with native collagen in adjacent sites.

Collagen is also used for a variety of other medical purposes. For example, collagen is used in sutures which can be naturally degraded by the human body and thus do not have to be removed following recovery. A sometimes limiting factor in the design of collagen sutures is the strength of the collagen fibers. A synthetic or a naturally occurring collagen that has been modified to exhibit greater strength would aid in the usage of such collagen sutures by relieving this limitation.

Researchers have been working on ways to increase the triple helix stability of collagen. For example, they have prepared a synthetic collagen mimic by replacing Pro in the Xaa position or Hyp in the Yaa position with 4(R)Fluoroproline (Flp) greatly increasing triple helix stability. (See U.S. Pat. No. 5,973,112 to Raines, which is incorporated herein by reference in its entirety; Holmgren et. al. (1998); and Holmgren et. al., *Chem. Biol.* 6: 63-70 (1999)). In contrast, it has also been shown that replacing Pro or Hyp in the Yaa position with the diastereomer 4(S)-fluoroproline (flp) greatly decreases stability, see: Bretscher et. al., *J. Am. Chem. Soc.* 123:777-778 (2001).

Other synthetic collagen mimics with increased stability compared to the triple helix of the native collagen have been prepared. Such collagen variants include 4(S)-fluoroproline (flp) in the Xaa position of the triple helical collagen tripeptide having the formula (XaaYaa Gly)$_n$. This collagen mimic was found to have increased stability relative to the collagen-related triple helices (ProYaaGly)$_n$, (hypYaaGly)$_n$, and (HypYaaGly)$_n$. (See U.S. Pat. No. 7,122,521 to Raines et. al., which is incorporated herein by reference in its entirety).

Also, Raines et. al. has disclosed additional synthetic collagen mimics with a tripeptide unit having the formula (Xaa-Yaa-Gly)$_n$ where one of the positions Xaa or Yaa is a bulky, non-electron withdrawing proline derivative. For example, such tripeptides can have the formula: (Xaa-Flp-Gly)$_n$, where Xaa is (2S,4R)-4-alkylproline or a (2S,4R)-4-thioproline, where Flp is (2S,4R)-4-fluoroproline, and n is a positive integer. The alkylprolines suitable in the Xaa position include 4-methylproline, 4-ethylproline, 4-propylproline, 4-isopropylproline, or other longer alkylprolines. Alternatively, the Yaa position may also be (2S,4S)-4-alkyl proline or a (2S,4S)-4-thioproline. All of these synthetic collagens result in stronger more stable triple helixes than native collagen. (See U.S. Published App. No. 20070275897 to Raines et. al., also incorporated by reference herein in its entirety). Despite the recent advances in this field, the art continues to seek more desirable approaches to prepare a collagen having increased stability for use in biomaterials for the medical field, and in leather-related products prepared by the tanning industry.

BRIEF SUMMARY OF THE INVENTION

The present invention is broadly summarized as an isolated collagen polypeptide having a tripeptide having the formula (Pro-Yaa-Gly)n, where Yaa is any O-methylated amino acid residue, and n is a positive integer. Also disclosed are methods for stabilizing the collagen triple helix by covalently modifying through O-methylation the second position of the tripeptide in a natural or synthetic collagen thereby making it possible to design other residues for that position, which add stability. The strengthened collagen molecules may be used as or integrated into biomaterials suitable for the medical field or in leather-related products prepared by the tanning industry.

In another aspect, the collagen peptide that is subjected to an O-methylation reaction procedure is either naturally occurring collagen or de novo synthesized collagen.

In a related aspect, the native collagen peptide is made semi-synthetic by covalently modifying through O-methylation the hydroxyproline (Hyp) at the second position of the natural collagen tripeptide repeat. In a preferred aspect, the second position of the collagen tripeptide is (2S,4R)-4-methoxyproline (Mop), such that the tripeptide has the formula (ProMopGly)$_n$. In a related aspect, the "n" is at least 3, 7, and 10 tripeptide repeats or between 3 and 300 tripeptide repeats.

In a related aspect, a synthetic collagen peptide is prepared such that the amino acid at the second position of the collagen tripeptide repeat is O-methylated as described here. One aspect of this invention is a synthetic collagen tripeptide with the formula (ProYaaGly)$_n$. Yaa is any O-methylated amino acid, or alternatively any O-methylated hydroxyproline, such as, for example, (2S,4R)-4-methoxyproline (Mop). In a related aspect, the "n" is at least 3, 7, and 10 tripeptide repeats or between 3 and 300 tripeptide repeats.

Other suitable amino acids used for stabilizing either naturally occurring or synthetic collagen include, but are not limited to O-mono- and di-halogenated methylated prolines. Such halogenated O-methyl prolines include, for example, O-monofluoromethylproline, O-difluoromethylproline, O-monochloromethylproline and O-dichloromethylproline.

Yet another aspect of the invention is a method of making a semi-synthetic collagen. The method includes providing a natural collagen polypeptide, wherein the polypeptide comprises tripeptides of the formula: (Pro-Yaa-Gly)n, and wherein Yaa is hydroxyproline. The hydroxyproline of the natural collagen polypeptide is then covalently modified using a methylation reagent to make the semi-synthetic collagen, which has an O-methylated hydroxyproline at the Yaa position of the tripeptide repeat and wherein the collagen has increased stability relative to natural collagen. A preferred amino acid residue at the Yaa position is (2S,4R)-4-methoxyproline (Mop).

Yet another aspect of the invention is a method of making collagen of improved strength. The method includes providing a de novo synthesized collagen polypeptide, wherein the polypeptide comprises tripeptides of the formula: (Pro-Yaa-Gly)$_n$. The Yaa position of the collagen polypeptide is then covalently modified using a methylation reagent to make collagen having an O-methylated amino acid at the Yaa position, such that the modified collagen has increased stability relative to natural collagen. A preferred amino acid residue at the Yaa position is O-methylated hydroxyproline. In one aspect, the invention provides a novel, highly stable collagen molecule produced by the method described herein, for use as a component in artificial skin, as solder in tissue welding to speed healing of large wounds, or as a collagen substitute for use in biomedical devices (implants and prostheses) and nanotechnology (drug delivery, implantable electric sensors and nanowires).

Another aspect of this invention provides a single method to strengthen collagen fibers for use in the tanning industry, as collagen is a major component of leather.

Unless otherwise defined, all technical and scientific terms used herein have the same meaning as commonly understood by one of ordinary skill in the art to which this invention belongs. Although suitable methods and materials for the practice or testing of the present invention are described below, other methods and materials similar or equivalent to those described herein, which are well known in the art, can also be used.

Other objects, advantages, and features of the present invention will become apparent upon review of the specification, drawings, and claims.

DETAILED DESCRIPTION OF THE INVENTION

Figure 1:
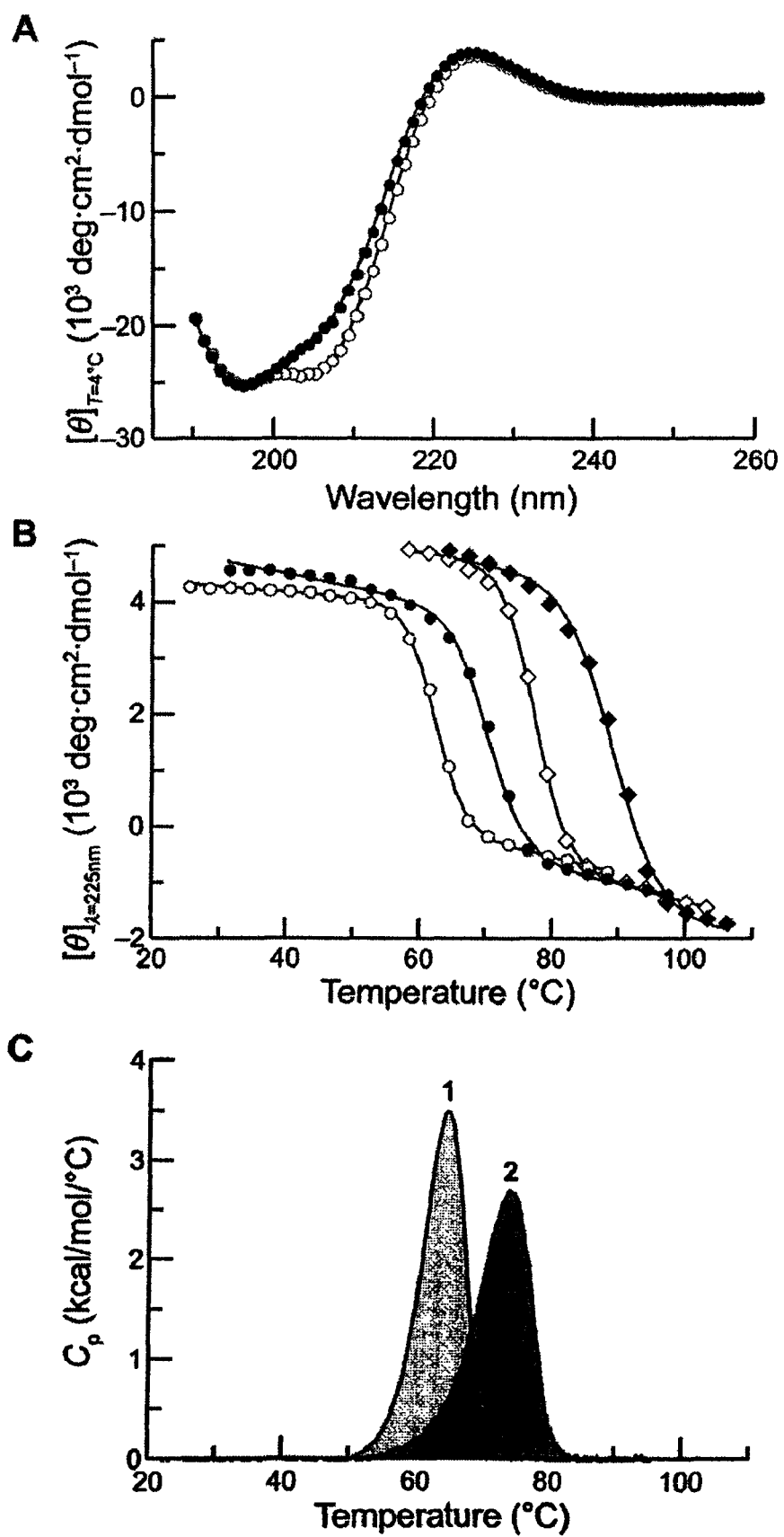
FIG. 1A-C shows a CD spectroscopy and DSC data for peptides 1 (ProHypGly)$_{10}$, and 2 (ProMopGly)$_{10}$. (A) CD spectra of 1 (○) and 2 (●) (100 μM) at 4° C. in 50 mM HOAc (pH 3.0). (B) Thermal denaturation of 1 and 2 (200 μM) in 50 mM HOAc(aq) (○,●) and 2:1 EG/50 mM HOAc (pH 3.0) (□, ■). (C) DSC scans of 1 (231 μM) and 2 (129 μM) in 50 mM HOAc (pH 3.0); scan rate=15° C./h.

The present invention broadly relates to an isolated collagen polypeptide designed to form a stronger triple helix than the native or natural collagen. The isolated collagen polypeptide has a tripeptide with the formula (Pro-Yaa-Gly)$_n$, where Yaa is any O-methylated amino acid residue, and n is a positive integer. The invention also relates to methods for stabilizing the collagen triple helix by covalently modifying the second position of a natural or synthetic collagen tripeptide. The covalent modification is done by O-methylating the second position of the collagen tripeptide. The methods of the invention make it possible to design other residues for the second position of the collagen tripeptide, resulting in added stability and strength to either a natural or synthetic collagen molecule. Such improved strength and stability enable the novel collagen substitute to be used as biomaterials in the medical field or in leather-related products prepared by the tanning industry.

In one embodiment of the invention, the second position of the natural collagen tripeptide repeat, which is hydroxyproline (Hyp), is covalently modified by O-methylating the hydroxyproline. A preferred amino acid at the second position is (2S,4R)-4-methoxyproline (Mop). Other suitable amino acids used for stabilizing synthetic or naturally occurring collagen include, but are not limited to O-mono- and di-halogenated methylated prolines. Such halogenated amino acids include, for example, O-monofluoromethylproline and O-difluoromethylproline. In addition to fluoromethyl groups, chloro derivatives, such as, monochloromethylproline and O-dichloromethylproline are suitable amino acids for increasing collagen stability.

In another embodiment, the collagen peptide that is subjected to an O-methylation reaction procedure is either naturally occurring collagen or collagen that is synthesized de novo.

In one embodiment, the collagen peptide is semi-synthetic, meaning that the Hyp in the second position of the tripeptide repeat of the natural collagen is O-methylated. In another embodiment, it is envisioned that synthetic collagen may be O-methylated to produce a highly stable collagen molecule for the uses described herein.

Another embodiment includes a composition of matter having a triple helix of collagen molecules in which each of the molecules in the helix has tripeptides of the formula (Pro-Yaa-Gly)$_n$, where Yaa is any modified O-methyl amino acid residue, and n is a positive integer. A preferred embodiment of the invention is where the collagen tripeptide has the formula (ProMopGly)$_n$.

As used here, the term "n" in the tripeptide repeat refers to a positive integer, such as at least 3, 7 and 10 tripeptide repeats or between 3 and 300 tripeptide repeats. It is generally accepted that if a modification of the Yaa position in the collagen tripeptide improves stability relative to the natural hydroxyproline (Hyp), it will do so for all tripeptide lengths (see Holmgen et. al. Nature 392:666-667 (1998), wherein n=10 and Bretscher et. al., J. Am. Chem. Soc., 123, 777-778 (2001), wherein n=7). Regardless of whether a tripeptide chain is made shorter or longer, in the inventor's experience, if stabilization by functionalized proline derivatives at the Yaa position is observed, it will continue to be observed over a range of peptide lengths. (See U.S. Pat. Nos. 5,973,112, 7,122,521 and U.S. Published App. No. 20070275897 to Raines et. al.)

Yet in another embodiment, the invention provides for a method of making a semi-synthetic collagen. The resultant collagen mimic exhibits increased stability relative to natural collagen such that it is suitable for use as a component in artificial skin, solder in tissue welding, or as a collagen substitute in other applications, requiring strong and stable biomaterials. The collagen variants with improved strength described here are also suitable for the tanning industry, as collagen is a major component of leather and related products.

The method includes alternatives for making highly stable and strong novel collagen molecules by providing a natural collagen polypeptide, wherein the polypeptide comprises tripeptides of the formula: (Pro-Yaa-Gly)$_n$, and wherein Yaa is hydroxyproline and n is at least 10 tripeptide repeats. The hydroxyproline of the natural collagen polypeptide is then covalently modified using a methylation reagent to make the semi-synthetic collagen, which has an O-methylated hydroxyproline at the Yaa position of the tripeptide repeat. The resultant collagen variant has increased stability relative to natural collagen.

As used here, the terms "polypeptide," "peptide" and "protein" are used interchangeably to refer to a polymer of collagen amino acid residues. The terms apply to amino acid polymers in which one or more amino acid residues is an artificial chemical mimetic of a corresponding naturally occurring amino acid, as well as to naturally occurring amino acid polymers and non-naturally occurring amino acid polymers.

As used here, the term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, alpha-carboxyglutamate, and O-phosphoserine. Amino acid analogs refers to compounds that have the same basic chemical structure as a naturally occurring amino acid, i.e., any carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

A suitable amino acid residue at the Yaa position of the collagen tripeptide is an O-methylated amino acid. More suitable amino acid residues include, for example, O-monofluoromethylproline and O-difluoromethylproline. Other halogenated methylprolines are also suitable for stabilizing a collagen tripeptide. A preferred amino acid residue at the Yaa position of the collagen tripeptide is (2S,4R)-4-methoxyproline (Mop).

Deuterated derivatives of the methoxygroup at the Yaa position of the collagen tripeptide, such as $OCH_2D$, $OCHD_2$ and $OCD_3$ may be used in preparing the tripeptides described herein.

As used here, the term "natural collagen" refers to any collagen protein or fragment thereof obtained from an animal source or expressed in native form via recombinant techniques.

As used here, the term "semi-synthetic collagen" is any natural collagen that is subsequently altered by synthetic modification.

As used here, the term "synthetic collagen" is a collagen-based peptide or polypeptide that is wholly synthesized in the laboratory from amino acids or other small molecule building blocks.

As used here, the term "de novo synthesis" refers to newly synthesized complex molecules like collagen polypeptides from simple chemical molecules, such as amino acids. Synthetic collagen is made by de novo synthesis as described in the examples below.

Theoretical and Experimental Strategies Involved in Designing Stronger Collagen Peptides.

The investigation that lead to the work described here, began with the notion that a better understanding of the factors that contribute to the three dimensional structure and stability of collagen would facilitate the design of a collagen variant having improved strength for use in wound healing, and the development of treatments for people suffering from collagen-related illnesses. It would also provide a stronger, more stable general purpose collagen for a variety of purposes, and industries, including but not limited to the tanning industry for strengthening collagen, a major component of leather.

The hypothesis underlying this study was the belief that bridging water molecules are unlikely to contribute significantly to collagen stability. First, immobilizing one or more water molecules for each Hyp residue would evoke an enormous entropic cost. A water molecule can form 4 hydrogen bonds. In bulk aqueous solution, these 4 hydrogen bonds are formed with other water molecules that are themselves mobile. In contrast, the bridging water molecules of collagen would suffer a far greater loss of entropy because two of their hydrogen bonds would be with collagen, which is immobile relative to a water molecule.

Second, if the bridging water molecules of collagen are indeed important for collagen stability, then it is likely that they would be homogeneous, with one hydrogen-bonding pattern predominating. However, a high-resolution three-dimensional structure of triple-helical collagen suggested that individual Hyp residues bond to 1, 2, 3, or 4 water molecules, forming irregular, complex networks of intrachain or interchain hydrogen bonds, Bella et al., *Science*, 266:75-81 (1994). This heterogeneity and complexity in the hydrogen bonding is inconsistent with the hypothesis that bridging water molecules confer stability to collagen.

Third, it is understood that the pucker of a pyrrolidine ring can be influenced by electronegative substitutents. This effect is stereoelectronic, as it depends on the configuration and electron-withdrawing ability of the substituent. In particular, the gauche effect exerted by an electron-withdrawing 4(R)-substituent stabilizes the Cγ-exo pucker, and that by a 4(S)-substituent stabilizes the Cγ-endo pucker. The degree of stabilization is greatest for fluorine, the most electronegative of atoms.

Furthermore, molecular modeling of a triple helix of (ProProGly)$_{10}$ strands has suggested that Pro in the Xaa and Yaa position prefers to adopt a Cγ-endo and Cγ-exo pucker, respectively. This pattern has been observed in the structure of a crystalline (ProProGly)$_{10}$ triple helix. The pyrrolidine ring pucker influences the range and distribution of the ø and ψ main-chain dihedral angles of Pro, and can fix those dihedral angles for optimal packing of the triple helix. Increasing the preference for the desired Cγ-exo conformation in the Yaa position by inclusion of either Hyp or Flp decreases the entropic penalty for triple-helix formation. Likewise, Hyp and Flp increase the preference of the ω main-chain dihedral angle for the trans (ω=180°) conformation. Because all of the peptide bonds in collagen are trans, preorganization of ω by Hyp and Flp decreases the entropic penalty for triple-helix formation.

As in the Yaa position, preorganization of ω in the trans conformation would also be favorable in the Xaa position. Yet, a Cγ-exo conformation favors o and v dihedrals that are not ideal for this position. Hence, fixing the ring pucker of proline in the Xaa position could have a favorable influence on either ø, ψ or ω, but not all three.

The results obtained through these molecular modeling studies have been advanced by independent laboratory results obtained where Pro or Hyp in the Yaa position was replaced with 4(R)-fluoroproline (Flp), leading to greatly increased triple helix stability, see U.S. Pat. No. 5,973,112 to Raines. It is understood that this gain in stability results from the greater preference of Hyp and Flp to adopt Cγ-exo ring puckers due to stereoelectronic effects. In contrast, replacing Pro or Hyp in the Yaa position with the diastereomer 4(S)-fluoroproline (flp) greatly decreases collagen stability, see: Bretscher et. al., *J Am. Chem. Soc.*, 123, 777-778 (2001).

To differentiate between these hypotheses, perhaps the simplest of covalent modifications to Hyp, O-methylation, was prepared, and is analyzed here. Similar alkylations are known to decrease the hydration of alcohols, (Hine and Mookejee, *J Org. Chem.* 40:292-298 (1975)) nucleobases, (Zielenkiewicz et. al., *J. Solution Chem.* 27:235-243 (1998)) and phospholipids (Dyck et. al., *Phys. Chem. Chem. Phys.* 7:150-156 (2005)). Yet, O-methylation conserves the stereoelectronic effects of a hydroxyl group, as the electron-withdrawing (Janesko et. al., *J. Phys. Chem.* 107:1655-1663 (2003)) and hyperconjugative (Alabugin and Zeidan, *J. Am. Chem. Soc.* 124:3175-3185 (2002)) ability of OH and $OCH_3$ are similar. Moreover, the O-methylation of Hyp introduces less steric encumbrance than does O-acetylation, which is known to destabilize the collagen triple helix (Jenkins et. al., *Biopolymers* 80:1-5 (2005)).

To further evaluate stabilization of the collagen triple helix by O-methylation of hydroxyproline residues, (2S,4R)-4- methoxyproline (Mop) (Krapcho et. al., *J. Med. Chem.* 31:1148-1160 (1998)) was synthesized and incorporated into a collagen-related peptide: (ProMopGly)$_{10}$ (peptide 2 of FIG. 1). Commercial (ProHypGly)$_{10}$ (peptide 1 of FIG. 1) was used as a basis for comparison. Circular dichroism (CD) spectroscopy was used to discern the effect of O-methylation. Peptides 1 and 2 were observed to form a triple helix at 4° C., as evidenced by a weak positive CD signal near 225 nm and a strong negative signal near 200 nm (FIG. 1A). In addition, both were found to undergo cooperative transitions upon heating (FIG. 1B), indicative of an unfolding triple helix. Most interestingly, triple helices of 2 were discovered to have substantially more conformational stability than those of 1 (Table 1). As in water, triple helical peptide 2, 2$_3$, was found to be more stable than triple helical peptide 1, 1$_3$, in aqueous ethylene glycol (EG; FIG. 1B, Table 1), which is known to stabilize the collagen triple helix. (Feng et. al., *J. Am. Chem. Soc.* 118:10351-10358 (1996)). Next, differential scanning calorimetry (DSC) was used to reveal the thermodynamic basis for the greater conformational stability of triple-helical peptide 2. The stability of 1$_3$ relies more on enthalpy and less on entropy than does that of triple-helical (ProFlpGly)$_{10}$ (peptide 3 of Table 1), indicative of a lesser reliance on a water network (Nishi et. al., *Biochemistry* 44:6034-6042 (2005)). The thermodynamic parameters for 2$_3$ lie between those for 1$_3$ and 3$_3$ (FIG. 1C; Table 1), suggesting that 2$_3$ is hydrated to an intermediate extent. The decrease in hydration and increase in conformational stability in the series 1$_3$→2$_3$→3$_3$ is consistent with hydration being deleterious, rather than advantageous, to the collagen triple helix.

TABLE 2

Values of φ, ψ, ω, and K$_{t/c}$ for Ac-Mop-OMe and analogs.

| parameter | Ac-Mop-OMe | Ac-Hyp-OMe[a] | Ac-Flp-OMe[a] | 1$_3$[b] |
|---|---|---|---|---|
| φ(°) | −58.1 ± 0.1 | −57.0 | −55.0 | −59.6 |
| ψ(°) | 147.7 ± 0.1 | 150.8 | 140.5 | 149.8 |
| ω(°) | −179.7 ± 0.1 | −178.8 | −178.9 | 178.5 |
| K$_{t/c}$ | 6.7 ± 0.3[c] | 6.1 | 6.7 | ∞ |

[a]Mean values of φ, ψ, and ω from two molecules in ref 18; values of K$_{t/c}$ from Bretscher et. al. (2001).
[b]Mean values for Hyp in 1$_3$ (Bella et. al, Science 266: 75-81 (1994); Miles and Burjanadze, Biophys. J. 80: 1480-1486 (2001)).
[c]Determined in 94: 6 D$_2$O/CD$_3$OD by $^{13}$C NMR spectroscopy using [$^{13}$CH$_3$]Ac-Mop-OMe.

Accordingly, this invention is based on the premise that the conformational stability conferred upon the collagen triple helix by O-methylation is evidence that the hydroxyl group of Hyp acts primarily through stereoelectronic effects and that its hydration provides little (if any) benefit. This finding could have practical consequences. Replacing a hydroxyl group in a protein with a fluoro group while retaining stereochemical configuration (as in Hyp→Flp) is not possible with extant reagents. In contrast, O-methylation of hydroxyproline at the Yaa position is a readily achievable transformation. Moreover, Hyp is much more abundant in human collagens than are the other two amino acids containing a hydroxyl group, Ser and Thr, (Ramshaw, J. A. M. et al., *J. Struct. Biol.* 122:86-91 (1998)) and host-guest studies indicate that Ser and Thr are not especially beneficial to collagen stability. (Persikov, A. V.,

TABLE 1

Thermodynamic data for the unfolding of collagen triple helices

| | | circular dichroism | | DSC | | |
|---|---|---|---|---|---|---|
| Peptide | Sequence | T$_m$, water[a] (° C.) | T$_m$, EG(aq)[b] (° C.) | ΔH (kcal/mol) | TΔS (kcal/mol) | ΔG (kcal/mol) |
| 1 | (ProHypGly)$_{10}$ | 62.0 | 77.1 | −35.2[c] | −33.2[c] | −2.0[c] |
| 2 | (ProMopGly)$_{10}$ | 70.1 | 89.1 | −27.9 | −25.2 | −2.7 |
| 3 | (ProFlpGly)$_{10}$ | 91[d] | ND | −20.5[c] | −17.2[c] | −3.3[c] |

[a]50 mM HOAc (pH 3.0),
[b]2:1 EG/50 mM HOAc (pH 3.0).
[c]Values from Nishi et. al., Biochemistry 44: 6034-6042 (2005).
[d]Value from Holmgen et. al. Nature 392: 666-667 (1998).
ND = Not determined.

Next, the effect of the methoxy group on the conformation of a Mop residue was determined. To do so, the model compound Ac-Mop-OMe was synthesized and its crystal structure was determined (FIG. 2A). The structure indicates that the pyrrolidine ring of Mop adopts a C$^\gamma$-exo ring pucker, which is likely derived from a gauche effect between N$_i$ and O$^{\delta 1}_i$ (Bretscher et. al., 2001). In addition, the conformation of Ac-Mop-OMe appears to rely on another stereoelectronic effect—the O$_{i-1}$ ... C′$_i$=O$_i$ distance of 2.84 Å and O$_{i-1}$ ... C′$_i$=O$_i$ angle of 94.6°, which indicate a favorable n→π* interaction (FIG. 2B). This stereoelectronic effect would stabilize the trans (Z) isomer of the amide bond in Ac-Mop-OMe. Indeed, Ac-Mop-OMe has a trans:cis ratio of K$_{t/c}$=6.7 (Table 2), which is among the largest reported in a derivative of Ac-Pro-OMe (Raines (2006)). Thus, these two stereoelectronic effects appear to preorganize the main-chain dihedral angles of Ac-Mop-OMe (as well as Ac-Hyp-OMe, and Ac-Flp-OMe) close to those in 1$_3$ (Table 2).

et al., *Biochemistry* 39:14960-14967 (2000)). It is believed that placing an O-methylated hydroxyproline at the Yaa position is a simple way to stabilize natural collagen, and thereby enhance its utility as a biomaterial. (Ramshaw, J. A. M., et al., (1995)). The intelligent design of improved collagen peptides is enabled for the first time. Other forms of collagen polypeptides having other amino acids at the second position (Yaa) in the triple helix motif are contemplated here.

Surprisingly, it was found that contrary to the results obtained from the O-methylation data, the addition of ethoxyproline (Eop) in (ProEopGly)$_{10}$ is less stable than Hyp (or Mop). This decreased stability may be due to the greater size or hydrophobicity of ethyl versus methyl groups. The impact of extending the alkyl chain on triple-helix stability was examined by studying (ProEopGly)$_{10}$ (Eop=(2S,4R)-4-ethoxyproline). The ethoxy group is more hydrophobic and less well hydrated than methoxy, so the low Tm of the ethoxy group may undermine the notion that triple-helix hydration is unfavorable for stability. However, the large solvent-exposed hydrophobic surface of an Eop-containing triple helix must be considered. Each triple helix of (ProEopGly)$_{10}$ displays 30 ethyl groups to the surrounding water, resulting in an additional 870 Å$^2$ (29 Å$^2$ per CH$_2$ (Sharp, K. A. et al., Science 252:106-109 (1991)) of hydrophobic surface compared to (2)$_3$. This forced hydrocarbon-water interaction likely has a detrimental effect on the entropy of the system, thus destabilizing the helix.

This shows that apparently there is a limit on alkyl chain length for triple helices in water; helices decorated with longer and/or more hydrophobic groups will likely be destabilized by the effects discussed above. It is also noted that Acetylation of Hyp proved slightly destabilizing, but not to the extent of ethylation (applicants' unpublished results). The acetyl group, although also comprising two carbons, is less hydrophobic and, most importantly, more electron withdrawing, thus increasing stereoelectronic effects.

In the examples below, the collagen mimics that were synthesized and tested had an O-methylated hydroxyproline residue at position Yaa. It is anticipated that amino acids other than the disclosed proline derivatives would be tolerated in the Yaa position, given that natural collagen has a wide variety of amino acids in the Yaa position. Hydroxyproline would be the prototypical residue at that position. The residues in the Yaa position can be the same or can vary in identity along a single collagen molecule.

The examples below describe among others the chemical synthesis of a collagen having the sequence (ProMopGly)$_{10}$. The number of repeats of this motif can be at least three, seven or ten, alternatively, the entire collagen can be constructed from this tripeptide, which is 300 tripeptide repeats in length. The present invention is intended to encompass a collagen tripeptide molecule having the described sequence, regardless of the mode of synthesis. It is anticipated that one skilled in the art of synthesizing biopolymers could make the peptide by using a modification of the chemical synthesis described below. The molecule can be made by direct synthesis, as described below.

Also, the collagen polypeptide has a ProYaaGly tripeptide repeat, suitably (ProMopGly)$_{10}$ prepared via the method of making collagen mimics described here below and in the inventors' related publication: Kotch et. al. J. Am. Chem. Soc. 130:2952-2953 (2008) and related supplementary information. Also, collagen polypeptides obtained by chemical and stereoelectronic modification of natural collagens are within the spirit and scope of the present invention.

EXAMPLES

Materials and Methods

Chemicals were from Aldrich or Acros (reagent grade or better), and were used without further purification. Amino acids were from Novabiochem, with the exception of Boc-Hyp-OH, which was from Chem-Impex International (Wood Dale, Ill.). (ProHypGly)$_{10}$.10H$_2$O was from Peptides International (Louisville, Ky.). Anhydrous DMF and CH$_2$Cl$_2$ were obtained from a CYCLE-TAINER® solvent delivery system from J. T. Baker (Phillipsburg, N.J.). All other solvents were from Fisher Scientific (Pittsburgh, Pa.). Flash chromatography was performed with columns of silica gel 60, 230-400 mesh (Silicycle, Québec City, QC, Canada). Semi-preparative HPLC was performed with a Zorbax C8 reversed-phase column and analytical HPLC was performed with an Agilent C8 reversed-phase column. Linear gradients of solvent A (H$_2$O with 0.1% v/v TFA) and solvent B (CH$_3$CN with 0.1% v/v TFA) were used for HPLC analysis and purification.

The removal of solvents and other volatile materials "under reduced pressure" refers to the use of a rotary evaporator at water-aspirator pressure (<20 torr) and a water bath of <40° C. Residual solvent was removed from samples at high vacuum (<0.1 torr). The term "high vacuum" refers to vacuum achieved by a mechanical belt-drive oil pump.

NMR spectra were recorded on either a Bruker DMX-400 Avance spectrometer or a Bruker DMX-500 Avance spectrometer at the National Magnetic Resonance Facility at Madison, Wis. (NMRFAM). Some compounds with a carbamate protecting group exist as mixtures of rotomers that do not interconvert on the NMR time scale at ambient temperatures and therefore exhibit two sets of NMR signals (as indicated).

Mass spectrometry was performed with either a Micromass LCT (electrospray ionization, ESI) in the Mass Spectrometry Facility in the University of Wisconsin Department of Chemistry or an Applied Biosystems Voyager DE-Pro (matrix-assisted laser desorption/ionization, MALDI) mass spectrometer in the University of Wisconsin Biophysics Instrumentation Facility.

Fmoc-Pro-Mop-Gly-OH was synthesized in 6 steps (overall yield: 30%) by the route shown in below.

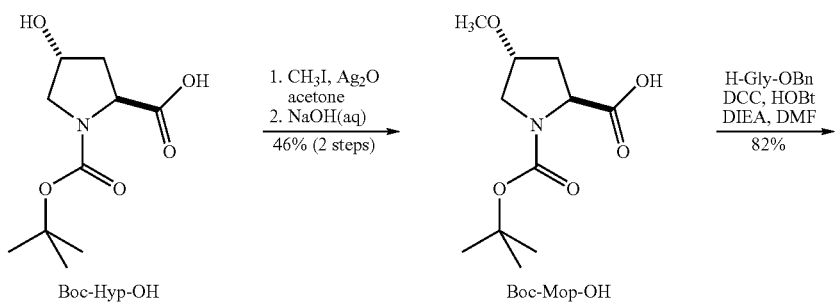

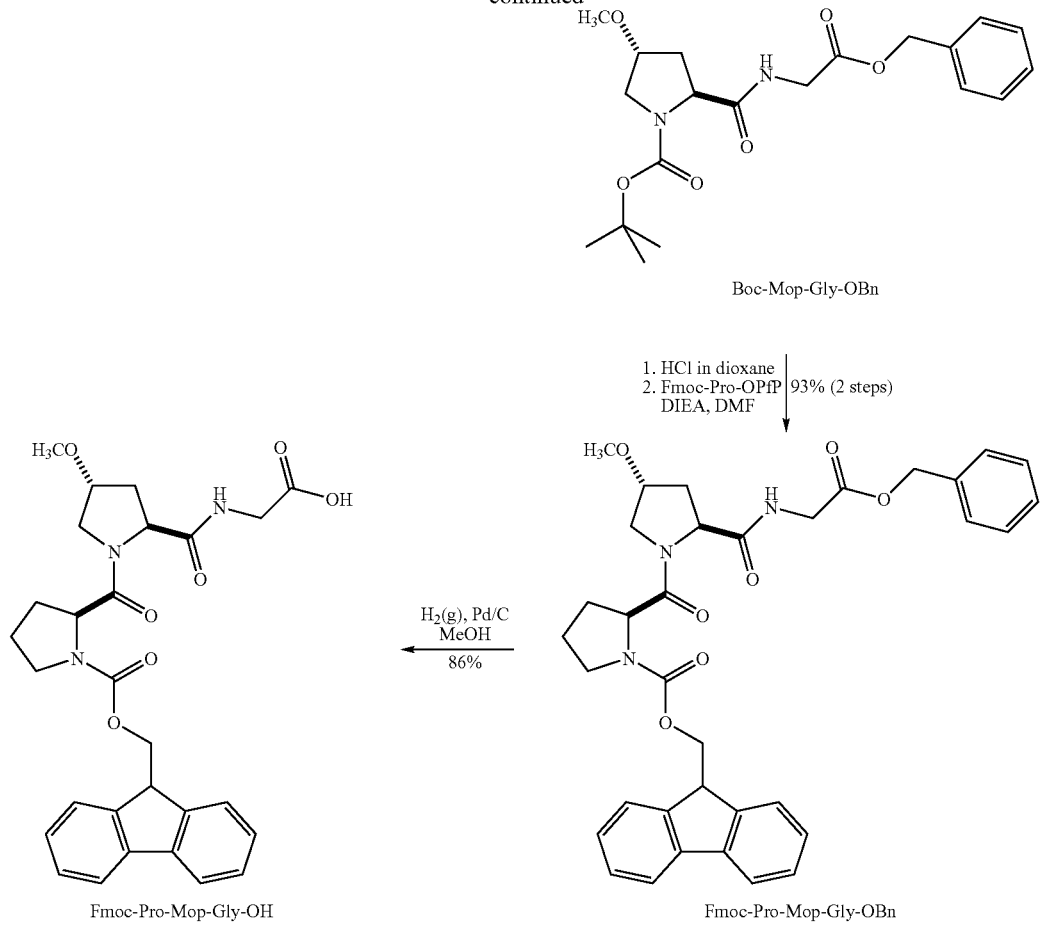

N-tert-Butoxycarbonyl-(2S,4R)-4-methoxyproline (Boc-Mop-OH)

This preparation is similar to that reported by Krapcho et. al. for Cbz-Mop-OH. (Krapcho et. al. *J. Med. Chem.* 31:1148-1160 (1988)). To a solution of N-tert-Butoxycarbonyl-(2S, 4R)-4-hydroxyproline (Boc-Hyp-OH, 2.00 g, 8.65 mmol) and $CH_3I$ (1.90 mL, 30.3 mmol) in acetone (50 mL) was added $Ag_2O$ (6.50 g, 28.1 mmol). The vessel was purged with Ar(g) and sealed with a septum, and the resulting suspension was stirred at room temperature for 24 h. The mixture was filtered and evaporated to a residue under reduced pressure. The residue was dried under high vacuum for 1 h, and then resubmitted to the reaction conditions a second time. After filtering and evaporating, the residue was dissolved in $H_2O$ (60 mL), a solution of NaOH (0.36 g, 9.08 mmol) in 1 mL $H_2O$ was added, and the solution was stirred at room temperature for 24 h (to hydrolyze any methyl ester that might have formed during alkylation). The aqueous mixture was acidified to pH 1 by the addition of 3 N HCl(aq) and extracted with $CH_2Cl_2$ (3×60 mL). The combined organic layers were dried over $MgSO_4$(s) and evaporated under reduced pressure, and the product was then isolated by flash chromatography (100:0-95:5 $CH_2Cl_2$/MeOH) affording Boc-Mop-OH (0.97 g, 46%) as a tinted residue. $^1H$ NMR (500 MHz, $CDCl_3$, ~3:2 ratio of 2 rotamers): δ 4.44 (t, J=7.5 Hz, 0.6 H), 4.34 (t, J=7.9 Hz, 0.4 H), 4.01-3.95 (m, 1 H), 3.70-3.65 (m, 0.4 H), 3.60-3.52 (m, 1 H), 3.49 (dd, J=11.7, 4.8 Hz, 0.6 H), 3.33 (overlapping s, 3 H), 2.46-2.36 (m, 1 H), 2.32-2.24 (m, 0.6 H), 2.17-2.07 (m, 0.4 H), 1.49 (s, 5.4 H), 1.43 (s, 3.6 H);

$^{13}C$ NMR (125 MHz, $CDCl_3$, ~3:2 ratio of 2 rotamers): δ 178.9, 176.0, 156.1, 154.0, 81.7, 80.9, 78.4, 78.2, 57.9 (2 signals), 56.9 (2 signals), 51.8, 51.0, 36.4, 34.3, 28.5, 28.4; HRMS (ESI): m/z calculated for $C_{11}H_{19}NO_5Na$ ($[M+Na]^+$) 268.1161, found 268.1151.

N-tert-Butoxycarbonyl-(2S,4R)-4-methoxyprolylglycine Benzyl Ester (Boc-Mop-Gly-OBn)

A solution of Boc-Mop-OH (0.42 g, 1.71 mmol), H-Gly-OBn.TsOH (0.64 g, 1.88 mmol), DCC (0.35 g, 1.71 mmol), $HOBt.H_2O$ (0.26 g, 1.71 mmol) and DIEA (0.89 mL, 5.13 mmol) in DMF (30 mL) was stirred at room temperature under Ar(g) for 20 h. The mixture was filtered to remove insoluble DCU and concentrated by rotary evaporation under high vacuum. The product was isolated by flash chromatography (two columns were needed; the first was run in 8:2 EtOAc/hexanes and the second in 7:3 EtOAc/hexanes) affording Boc-Mop-Gly-OBn (0.55 g, 82%) as a clear oil. $^1H$ NMR (500 MHz, $CDCl_3$, ~3:2 ratio of 2 rotamers): δ7.41-7.32 (m, 5 H), 6.53 (app bs, 0.4 H), 5.22-5.15 (m, 2 H), 4.44 (dd, J=7.9, 5.6 Hz, 0.6 H); 4.31 (t, J=7.8 Hz, 0.4 H), 4.16-3.97 (m, 2.6 H), 3.93 (app bs, 0.4 H), 3.81-3.72 (m, 0.6 H), 3.53-3.43 (m, 1.4 H), 3.32 and 3.31 (overlapping s, 3 H), 2.49-2.42

(m, 0.6 H), 2.41-2.33 (m, 0.4 H), 2.16-2.05 (m, 1 H), 1.89 (bs, 0.6 H), 1.47 (s, 5 H), 1.42 (s, 4 H); $^{13}$C NMR (125 MHz, CDCl$_3$, ~3:2 ratio of 2 rotamers): δ 173.0, 172.2, 169.8, 169.6, 156.0, 154.8, 135.3, 135.1, 128.8 (2 signals), 128.7, 128.6, 128.5, 81.1, 81.0, 78.7, 78.2, 67.5, 67.3, 60.0, 58.7, 57.0, 56.9, 51.7, 51.5, 41.6, 41.2, 36.8, 33.7, 28.5, 28.4; HRMS (ESI): m/z calculated for C$_{20}$H$_{28}$N$_2$O$_6$Na ([M+Na]$^+$) 415.1845, found 415.1852.

N-9-Fluorenylmethoxycarbonyl-(2S)-prolyl-(2S,4R)-4-methoxyprolylglycine Benzyl Ester (Fmoc-Pro-Mop-Gly-OBn)

Boc-Mop-Gly-OBn (0.54 g, 1.38 mmol) was dissolved in 14 mL of 4N HCl in dioxane (56 mmol) and the solution was stirred at room temperature under Ar(g) for 2.5 h. The mixture was evaporated under reduced pressure, the remaining white solid (H-Mop-Gly-OBn.HCl) was azeotroped twice with toluene and dried under high vacuum for 2 h. The solid was dissolved in DMF (20 mL), FmocPro pentafluorophenyl ester (0.69 g, 1.38 mmol) and DIEA (0.48 mL, 2.75 mmol) were added, and the mixture was stirred at room temperature under Ar(g) for 20 h. The mixture was concentrated by rotary evaporation under high vacuum, and the product was isolated by flash chromatography (9:1 EtOAc/hexanes) affording Fmoc-Pro-Mop-Gly-OBn (0.78 g, 93% over 2 steps) as a clear residue. $^1$H NMR (400 MHz, CDCl$_3$, mixture of 3 or more rotomers, integrations are approximate): δ 8.28 (t, J=6.1 Hz, 0.3 H), 7.78-7.72 (m, 2 H), 7.65-7.51 (m, 2 H), 7.45-7.28 (m, 8 H), 7.27-7.23 (m, 1H+CHCl$_3$), 7.21-7.18 (m, 1 H), 5.13 (app dd, J=22.4, 12.3 Hz, 1.3 H), 5.00 (app dd, J=25.5, 12.3 Hz, 0.7 H), 4.76 (dd, J=4.4, 4.0 Hz, 0.4 H), 4.63 (dd, J=4.4, 4.0 Hz, 0.2 H), 4.55-4.30 (m, 3.2 H), 4.28-4.07 (m, 2.6 H), 4.07-3.86 (m, 2.2 H), 3.76-3.46 (m, 4 H), 3.39 (dd, J=5.3, 5.0 Hz, 0.2 H), 3.34 (s, 1.3 H), 3.29 (s, 1 H), 3.21 (s, 0.6 H), 2.55-2.45 (m, 1 H), 2.44-2.36 (m, 0.4 H), 2.25-1.80 (m, 6 H); $^{13}$C NMR (100 MHz, CDCl$_3$, mixture of 3 or more rotomers): δ172.5 (2 signals), 172.1, 171.9, 171.5, 171.3, 169.6, 169.5, 169.3, 162.7, 155.5, 155.1, 154.8, 144.6, 144.3, 144.2, 144.0, 143.8, 141.5 (multiple signals), 135.4, 128.8, 128.7, 127.8 (multiple signals), 127.2, 125.4, 125.2, 125.1, 125.0, 120.1 (2 signals), 79.1, 79.0, 67.9, 67.6, 67.3, 67.2, 67.1, 59.6, 58.8, 58.6, 58.1, 58.0, 57.2, 57.1, 51.5, 51.0, 47.6, 47.4, 47.2 (2 signals), 46.9, 41.6, 41.5, 37.3, 32.5, 32.2, 30.5, 29.4 (2 signals), 24.8, 24.5, 23.3; HRMS (ESI): m/z calculated for C$_{35}$H$_{37}$N$_3$O$_7$Na ([M+Na]$^+$) 634.2529, found 634.2517.

N-9-Fluorenylmethoxycarbonyl-(2S)-prolyl-(2S,4R)-4-methoxyprolylglycine (Fmoc-Pro-Mop-Gly-OH)

A suspension of Fmoc-Pro-Mop-Gly-OBn (0.74 g, 1.21 mmol) and Pd/C (0.07 g) in MeOH (25 mL) was stirred under an atmosphere of H$_2$ (g) for 2 h. The mixture was filtered through a pad of Celite® and evaporated leaving a white solid. The product was isolated by flash chromatography (9:1 CH$_2$Cl$_2$/MeOH-EtOH) affording Fmoc-Pro-Mop-Gly-OH (0.54 g, 86%) as a white solid. $^1$H NMR (500 MHz, DMSO-d$_6$, ~1:1 ratio of 2 rotamers): δ7.91-7.82 (m, 2 H), 7.65 (t, J=7.4 Hz, 1 H), 7.58 (d, J=7.4 Hz, 0.5 H), 7.55 (d, J=7.5 Hz, 0.5 H), 7.44-7.28 (m, 5 H), 4.60 (dd, J=8.6, 3.1 Hz, 0.5 H), 4.52 (dd, J=8.6, 2.7 Hz, 0.5 H), 4.45-4.40 (m, 0.5 H), 4.34 (app t, J=7.4 Hz, 0.5 H), 4.27-4.10 (m, 3 H), 4.04-3.97 (m, 1 H), 3.76-3.70 (m, 0.5 H), 3.67-3.57 (m, 1.5 H), 3.42-3.29 (signals under H$_2$O peak), 3.22 (s, 1.5 H), 3.11 (s, 1.5 H), 2.32-2.29 (m, 0.5 H), 2.28-2.18 (m, 0.5 H), 2.17-2.06 (m, 1.5 H), 2.02-1.73 (m, 4.5H); $^{13}$C NMR (125 MHz, DMSO-d$_6$, ~1:1 ratio of 2 rotamers): δ171.7, 171.0, 170.3, 170.2, 153.8, 143.9 (3 signals), 143.8, 140.7, 140.6, 127.7 (2 signals), 127.2, 127.1, 125.3, 125.1, 120.1, 120.0 (2 signals), 78.6, 78.4, 66.8, 66.5, 58.3 (2 signals), 57.9, 57.6, 56.1, 56.0, 55.9, 51.3, 51.2, 47.0, 46.7, 46.6, 46.3, 42.0, 34.3, 29.6, 28.6, 23.7, 22.6;

HRMS (ESI): m/z calculated for C$_{28}$H$_{31}$N$_3$O$_7$Na ([M+Na]$^+$) 544.2060, found 544.2039.

N-(2-$^{13}$CH$_3$-Acetyl)-(2S,4R)-4-methoxyproline methyl ester (2-$^{13}$CH$_3$—Ac-Mop-OMe)

A solution of Boc-Mop-OH (100 mg, 0.41 mmol) in anhydrous MeOH (12.5 mL) was cooled to 0° C. Acetyl chloride (12.5 mL) was added dropwise over 5 min., the mixture was allowed to warm to room temperature and stirred under Ar(g) for 7 h. The solvent was evaporated under reduced pressure, and the resulting residue (H-Mop-OMe.HCl) was dried under high vacuum for 1 h. (See Nudelman, A., Synth. Commun. 1998, 28, 471-474.) The residue was dissolved in CH$_2$Cl$_2$ (20 mL), N,N-Dimethylaminopyridine (500 mg, 3.84 mmol) was added, followed by dropwise addition of H$_3$$^{13}$CC(O)Cl (273 mL, 3.84 mmol) and the mixture was stirred at room temperature under Ar(g) for 24 h. MeOH (5 mL) was added to quench the reaction. The mixture was concentrated under reduced pressure, the remaining residue was dissolved in CH$_2$Cl$_2$ (40 mL) and washed with 10% w/v aqueous citric acid. The aqueous layer was back-extracted with CH$_2$Cl$_2$ (3×20 mL), and the combined organic layers were dried over MgSO$_4$(s) and evaporated under reduced pressure. The product was isolated by flash chromatography (1:1 EtOAc/hexanes to elute byproducts followed by 94:6 EtOAc/MeOH) affording 2-$^{13}$CH$_3$—Ac-Mop-OMe (71 mg, 86%) as a white solid. $^1$H NMR (500 MHz, CDCl$_3$, ~4:1 ratio of trans:cis amide bond rotamers): δ4.50 (app t, J=7.8 Hz, 1 H), 4.11-4.07 (m, 0.8 H), 4.02-3.98 (m, 0.2 H), 3.96-3.91 (m, 0.2 H), 3.82-3.78 (m, 0.8 H), 3.79 (s, 0.6 H), 3.75 (s, 2.4 H), 3.58-3.51 (m, 1 H), 3.35 (s, 2.4 H), 3.32 (s, 0.6 H), 2.52-2.45 (m, 0.2 H), 2.40-2.32 (m, 0.8 H), 2.27-2.19 (m, 0.2 H), 2.11-2.03 (m, 0.8 H), 2.10 (d, J$_{C-H}$=128 Hz, 2.4 H), 1.97 (d, J$_{C-H}$=128 Hz, 0.6 H); $^{13}$C NMR (125 MHz, CDCl$_3$, 4:1 ratio of trans:cis amide bond rotamers): δ 173.0, 172.8, 170.2 (d, J=51 Hz), 169.6 (d, J=52 Hz), 79.0, 77.4, 58.8, 57.4, 56.9, 52.9, 52.5, 50.8, 37.3, 34.5, 22.5 and 21.9 (labeled $^{13}$C); HRMS (ESI): m/z calculated for C$_8$$^{13}$CH$_{15}$NO$_4$Na ([M+Na]$^+$) 225.0932, found 225.0925.

Attachment of Fmoc-Pro-Mop-Gly-OH onto 2-chlorotrityl chloride resin

Under Ar(g), 69 mg (0.110 mmol) of 2-chlorotrityl chloride resin (loading 1.6 mmol/g) was swollen in dry CH$_2$Cl$_2$ (0.4 mL). A solution of Fmoc-Pro-Mop-Gly-OH (40 mg, 0.077 mmol) in dry CH$_2$Cl$_2$ (1.0 mL) was added followed by DIEA (58 μL, 0.330 mmol), and the resin suspension was agitated gently for 2.5 h. Anhydrous CH$_3$OH (0.2 mL) was added to the mixture and the suspension was agitated for an additional 15 min (to cap any remaining active sites on the resin). The resin-bound peptide was isolated by gravity filtration, washed with dry CH$_2$Cl$_2$ (20×1 mL), and dried over KOH under high vacuum for 18 h. Loading was measured by UV spectroscopy using the reported protocol to be 0.57 mmol/g. (See Applied Biosystems Determination of the Amino Acid Substitution Level via an Fmoc Assay; Technical Note 123485 Rev 2; Documents on Demand—Applied Biosystems Web Page (Nov. 30, 2005)).

Peptide Synthesis.

(Pro-Mop-Gly)$_{10}$ was synthesized by segment condensation of Fmoc-Pro-Mop-Gly-OH on solid phase using an Applied Biosystems Synergy 432A Peptide Synthesizer at the University of Wisconsin—Madison Biotechnology Center. The first trimer was loaded onto the resin as described above. Fmoc-deprotection was achieved by treatment with 20% v/v piperidine in DMF. The Fmoc-tripeptides (3 equiv) were converted to active esters by treatment with HBTU, DIEA, and HOBt. Couplings were allowed to proceed for 45-60 min at room temperature. The peptide was cleaved from the resin in 38:1:1 TFA/H$_2$O/triisopropylsilane (1 mL), precipitated from tert-butylmethylether at 0° C., and isolated by centrifugation. Semi-preparative HPLC was used to purify (Pro-Mop-Gly)$_{10}$ (gradient: 10% B to 30% B over 60 min). The peptide was >90% pure by analytical HPLC and characterized by MALDI-TOF mass spectrometry: (m/z) [M+H]+ calculated for (Pro-Mop-Gly)$_{10}$ 2830.4. found 2831.3.

Circular Dichroism (CD) Spectroscopy.

CD spectra were recorded with an Aviv 202SF circular dichroism spectrometer. Spectra were recorded on peptide solutions (100 µM in 50 mM HOAc (pH 2.9)) that had been incubated at ≦4° C. for ≧48 h in 1-nm increments with a 3-s averaging time, 1-nm bandpass, and 0.1-cm pathlength. Samples for thermal stability experiments were generated by incubating peptide solutions (200 µM) at 4° C. for ≧48 h. The solutions were then heated from 4° C. to 97° C. (for samples in 50 mM HOAc (aq) (pH 2.9)) or to 106° C. (for samples in 2:1 ethylene glycol/50 mM HOAc(aq)) at 3-° C. increments with a 5-min equilibration at each step. The ellipticity at 225 nm was monitored with a 5-s averaging time, 1-nm bandpass, and 0.1-cm pathlength. Values of $T_m$ were determined by fitting the data to a two-state model. (See Becktel and Schellman *Biopolymers* 26:1859-1877 (1987)).

Differential Scanning Calorimetry (DSC).

DSC measurements were conducted on a VP-DSC instrument (MicroCal, LLC, Northampton, Mass.). For each peptide, an instrument baseline was established by filling both the sample and the reference cell with degassed 50 mM HOAc (aq) (pH 2.9) and scanning from 5-98° C. at 15° C./h until at least 3 consecutive overlaying scans were observed. The last of these scans was used as the baseline for each subsequent peptide scan.

Peptide solutions (~0.5 mg/mL in 50 mM HOAc(aq)), incubated at 4° C. for ≧48 h, were degassed and loaded into the sample cell (without removing the reference solution) during the cool down from the final baseline scan (at ~15° C.). Samples were scanned from 5-98° C. at 15° C./h; the first scan of each sample was used in the analysis. Subsequent scans of the same sample showed a decreased melting enthalpy indicative of incomplete recovery of triple helix (60-80%); because complete helical folding of these peptides requires a few hours at low temperature, and the sample cells were cooled at ~15° C./min, incomplete folding is expected during the rapid cool down cycle. Nevertheless, a second run with a fresh sample (incubated at 4° C. for ≧48 h) gave a trace that overlaid with the initial scan for both peptides.

After DSC measurements, peptide concentrations were determined by quantitative amino acid analysis (Scientific Research Consortium, Inc., St. Paul, Minn.). Peptide concentrations of 231 µM for (ProHypGly)$_{10}$ and 129 µM for (Pro-MopGly)$_{10}$ were calculated from the average of Gly and Pro content.

Data processing was done using the MicroCal software in the Origin 7 program (OriginLab Corp., Northampton, Mass.). For each sample, the appropriate reference scan was subtracted from the sample scan and the data were normalized to the monomer concentrations (determined above). A progress baseline was then subtracted from the data, giving the traces shown in FIG. 1C.

Values of ΔH (per mole of monomer) were obtained by direct integration of the DSC exotherms. Using ΔH and the exotherm maxima as the $T_m$ (64.3° C. for (ProHypGly)$_{10}$ and 73.8° C. for (ProMopGly)$_{10}$), TΔS (at $T_m$) was calculated with the equation: $T_m=\Delta H/(\Delta S+R\cdot\ln(0.75c^2))$, where c is the concentration of monomeric peptide. (See Engel and Bäichinger P. *Top. Curr. Chem.* 247:7-33 (2005)). Values of ΔG were then calculated with the equation: ΔG=ΔH−TΔS. Table 1, provided herein, lists only data for (ProMopGly)$_{10}$, comparing these data to those reported by Kobayashi and coworkers for (ProHypGly)$_{10}$ and (ProFlpGly)$_{10}$. (See Nishi et. al. (2005)). The data of Kobayashi and coworkers were normalized to T°=71.9° C. (which is the T° for (ProProGly)$_{10}$, i.e. where ΔG=0). Because our thermodynamic data for (Pro-MopGly)$_{10}$ were determined at nearly the same temperature (73.8° C.), comparisons of the three peptides are meaningful.

The values for (ProHypGly)$_{10}$, however, were determined at 64.3° C., and such comparisons become unsound with larger differences in temperature. For (ProHypGly)$_{10}$, the thermodynamic parameters at 64.3° C. were ΔH=−29.5 kcal/mol, TΔS=−27.3 kcal/mol, and ΔG=−2.2 kcal/mol. Note that AG agrees with that reported by Kobayashi and coworkers (−2.0 kcal/mol).

Measurement of the Amide Bond Trans/Cis Equilibrium Constant ($K_{t/c}$) in [$^{13}$CH$_3$]Ac-Mop-OMe.

[$^{13}$CH$_3$]Ac-Mop-OMe (10 mg) was dissolved in 94:6 D$_2$O/CH$_3$OD (850 µL). The $^{13}$C NMR spectrum was recorded using an inverse gated decoupling pulse program with a relaxation delay of 60 s and a pulse width of 10 µs. A total of 32 transients were collected. The spectral baseline was corrected and peaks corresponding to the labeled carbon were integrated with the software package NUTS. (See NUTS—NMR Utility Transform Software, Acorn NMR, Inc., 7670 Las Positas Road, Livermore, Calif. 94551.) Values of $K_{t/c}$ were determined by the relative areas of the trans and cis peaks for the labeled carbon.

Crystallization of Ac-Mop-OMe.

[$^{13}$CH$_3$]Ac-Mop-OMe (10 mg) was dissolved in 1:1 CH$_2$Cl$_2$/hexanes (1 mL) and the solution was allowed to stand at room temperature in a loosely-capped vial. Slow evaporation afforded crystals suitable for X-ray analysis after ~72 h (all solvent had evaporated).

Crystallographic Data Collection.

A colorless crystal with approximate dimensions 0.49× 0.41×0.23 mm$^3$ was selected under oil under ambient conditions and attached to the tip of a nylon loop. The crystal was mounted in a stream of cold N$_2$ (g) at 100(2) K and centered in the X-ray beam by using a video camera.

The crystal evaluation and data collection were performed on a Bruker CCD-1000 diffractometer with Mo K$_\alpha$ (λ=0.71073 Å) radiation and the diffractometer-to-crystal distance of 4.9 cm.

The initial cell constants were obtained from three series of scans at different starting angles. Each series consisted of 20 frames collected at intervals of 0.3° in a 6° range about ω with the exposure time of 10 s per frame. A total of 69 reflections were obtained. The reflections were indexed successfully by an automated indexing routine built in the SMART program. The final cell constants were calculated from a set of 4805 strong reflections from the actual data collection.

Data were collected by using the full-sphere data collection routine. The reciprocal space was surveyed to the extent of a full sphere to a resolution of 0.80 Å. A total of 6155 data were harvested by collecting three sets of frames with 0.3° scans in ω and χ with an exposure time 10 s per frame. These highly redundant datasets were corrected for Lorentz and polarization effects. The absorption correction was based on fitting a function to the empirical transmission surface as sampled by multiple equivalent measurements. (Bruker-AXS. (2000-2003) SADABS V.2.05, SAINT V.6.22, SHELXTL V.6.10 & SMART 5.622 Software Reference Manuals. Bruker-AXS, Madison, Wis., USA.)

Crystallographic Structure Solution and Refinement.

The systematic absences in the diffraction data were consistent for the space groups $P2_1$ and $P2_1/m$. The E-statistics strongly suggested the non-centrosymmetric space group $P2_1$ that yielded chemically reasonable and computationally stable results of refinement.

A successful solution by the direct methods provided most non-hydrogen atoms from the E-map. The remaining non-hydrogen atoms were located in an alternating series of least-squares cycles and difference Fourier maps. All non-hydrogen atoms were refined with anisotropic displacement coefficients. All hydrogen atoms were found in the difference map and refined independently. The absolute configuration was assigned from the known synthetic procedure.

Figure 2:
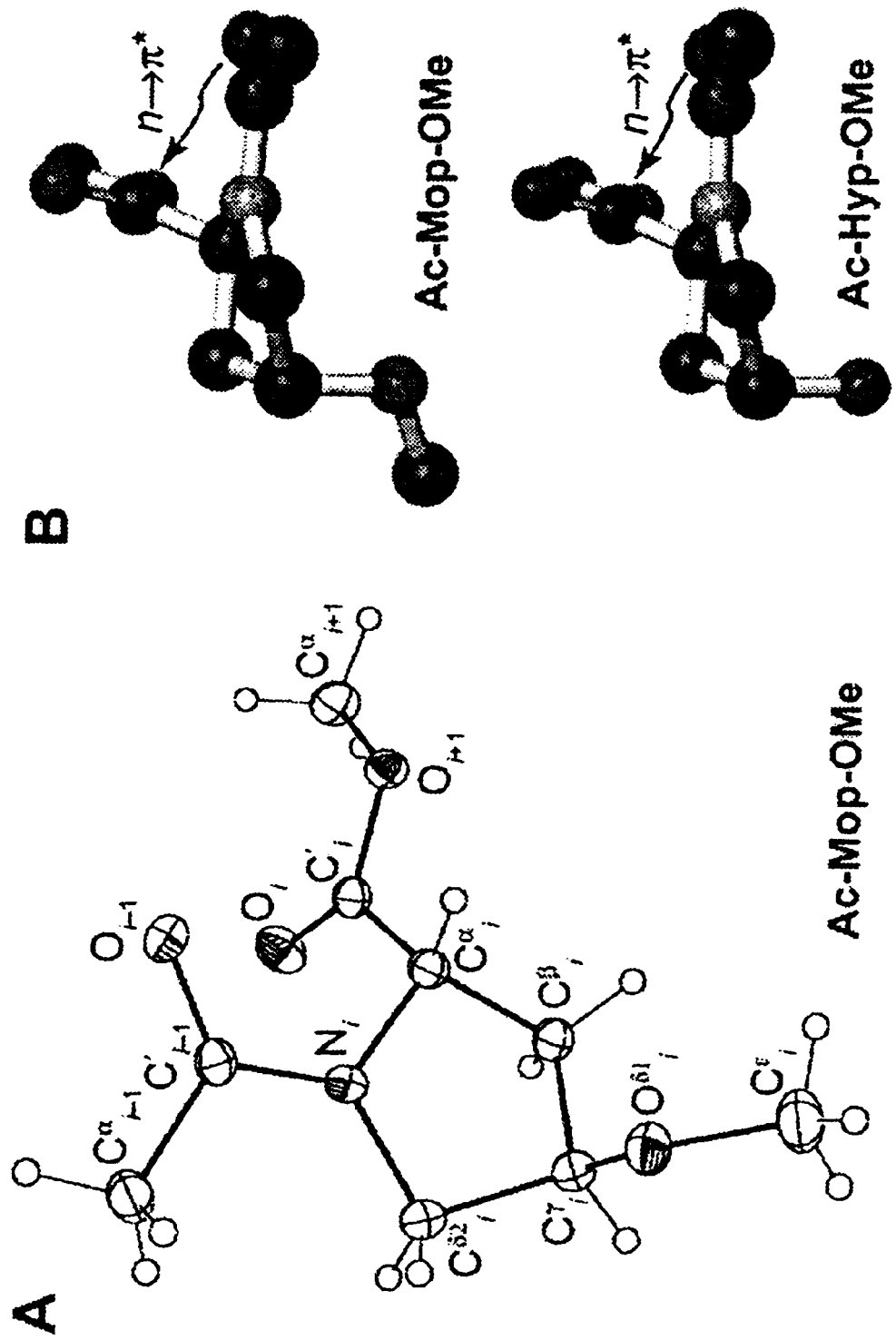
FIG. 2A-C shows (A) molecular drawing of crystalline Ac-Mop-OMe (50% probability ellipsoids); (B) Conformation of crystalline Ac-Mop-OMe and (C) Ac-Hyp-OMe showing the putative n→π* interaction.

The final least-squares refinement of 187 parameters against 2089 data resulted in residuals R (based on $F^2$ for $I \geq 2\sigma$) and wR (based on $F^2$ for all data) of 0.0273 and 0.0706, respectively. The final difference Fourier map was featureless. The molecular diagram is drawn with 50% probability ellipsoids as depicted in FIG. 2.

The disclosure of every patent, patent application, and publication cited herein is hereby incorporated herein by reference in its entirety.

It is understood that certain adaptations of the invention described in this disclosure are a matter of routine optimization for those skilled in the art, and can be implemented without departing from the spirit of the invention, or the scope of the appended claims.

We claim:

1. An isolated collagen polypeptide comprising a tripeptide having the formula:
   (Pro-Yaa-Gly)$_n$,
   where Yaa is any O-methylated amino acid residue, and "n" is a positive integer.

2. The polypeptide of claim 1, wherein Yaa is an O-methylated hydroxyproline.

3. The polypeptide of claim 1, wherein Yaa is (2S,4R)-4-methoxyproline (Mop).

4. The polypeptide of claim 1, wherein Yaa is an O-mono- or O-dihalogenated methylproline.

5. The polypeptide of claim 1, wherein Yaa is selected from a member of the group consisting of O-monofluoromethylproline, O-difluoromethylproline, O-monochloromethylproline, and O-dichloromethylproline.

6. The polypeptide of claim 1, wherein "n" is at least 3.

7. The polypeptide of claim 1, wherein "n" is at least 7.

8. The polypeptide of claim 1, wherein "n" is at least 10.

9. The polypeptide of claim 1, wherein "n" is between 3 and 300.

10. The polypeptide of claim 1, wherein the polypeptide is obtained from naturally occurring collagen that is covalently modified at the Yaa position or from de novo synthesized collagen.

11. An isolated collagen polypeptide comprising a tripeptide having the formula (ProMopGly)$_{10}$.

12. A method of making a semi-synthetic collagen, the method comprising the steps of:
   providing a natural collagen polypeptide, wherein the polypeptide comprises tripeptides of the formula: (Pro-Yaa-Gly)$_n$, and wherein Yaa is hydroxyproline and "n" is a positive integer;
   covalently modifying the hydroxyproline of the natural collagen polypeptide using a methylation reagent to make a semi-synthetic collagen having an O-methylated hydroxyproline at the Yaa position, such that the semi-synthetic collagen has increased stability relative to natural collagen.

13. The method of claim 12, wherein the amino acid at the Yaa position is (2S,4R)-4-methoxyproline (Mop).

14. The method of claim 12, wherein "n" is between 3 and 300.

15. A semi-synthetic O-methylated collagen manufactured by the process of claim 12.

16. The method of claim 12, wherein the amino acid at the Yaa position is an O-mono- or O-dihalogenated methylproline.

17. A method of making synthetic collagen, the method comprising the steps of:
   providing a de novo synthesized collagen polypeptide, wherein the polypeptide comprises tripeptides of the formula: (Pro-Yaa-Gly)$_n$, wherein "n" is a positive integer;
   covalently modifying the Yaa position of the collagen polypeptide using a methylation reagent to make collagen having an O-methylated amino acid at the Yaa position, such that the modified synthetic collagen has increased stability relative to natural collagen.

18. The method of claim 17, wherein the O-methylated amino acid is O-methylated hydroxyproline.

19. The method of claim 17, wherein the O-methylated amino acid is (2S,4R)-4-methoxyproline (Mop).

20. The method of claim 17, wherein "n" is between 3 and 300.

21. The method of claim 17, wherein the amino acid at the Yaa position is an O-mono- or O-dihalogenated methylproline.

* * * * *